United States Patent [19]

Knight, III

[11] Patent Number: 4,520,031

[45] Date of Patent: May 28, 1985

[54] METHOD FOR REDUCING TOXIC EFFECTS OF METHYL-GLYOXAL BIS-GUANYLHYDRAZONE

[75] Inventor: William A. Knight, III, San Antonio, Tex.

[73] Assignee: The United States of America as represented by the Secretary of Department of Health and Human Services, Washington, D.C.

[21] Appl. No.: 410,965

[22] Filed: Aug. 24, 1982

Related U.S. Application Data

[63] Continuation-in-part of Ser. No. 268,670, Jun. 1, 1981, abandoned, which is a continuation of Ser. No. 128,200, Mar. 7, 1980, abandoned.

[51] Int. Cl.$^3$ ............................................ A61K 31/155
[52] U.S. Cl. ............................................................ 514/632
[58] Field of Search ........................................ 424/326

[56] References Cited

PUBLICATIONS

Boiron et al., Cancer Chemotherapy Reports No. 45, Apr., 1965, pp. 69–73.
Knight, III et al., Cancer Treatment Reports, vol. 63, No.-11–12, Nov./Dec. 1979, pp. 1933–1937.

*Primary Examiner*—Jerome D. Goldberg
*Attorney, Agent, or Firm*—John S. Roberts, Jr.

[57] ABSTRACT

A method of treating cancers or advanced malignant disease involving the weekly administration of methyl-glyoxal bis-guanylhydrazone in amounts of 250–1,000 mg/m$^2$ per week. In particular the administration involves a weekly dosing regimen and dose escalation over the series of treatments from an initial dosage which may be 250 mg/m$^2$.

3 Claims, No Drawings

METHOD FOR REDUCING TOXIC EFFECTS OF METHYL-GLYOXAL BIS-GUANYLHYDRAZONE

The invention described herein was made in the course of work under a grant or award from the Department of Health and Human Services.

This is a continuation-in-part application of pending Ser. No. 268,670 filed June 1, 1981, now abandoned, which is a continuation application of Ser. No. 128,200 filed Mar. 7, 1980, now abandoned.

FIELD OF THE INVENTION

The present invention relates to a method of treating cancer or advanced malignant disease with methyl-glyoxal bis-guanylhydrazone. In particular, this invention relates to the periodic administration of methyl-glyoxal bis-guanylhydrazone to individuals with cancer.

PRIOR ART STATEMENT

Boiron, *Cancer Chemotherapy Reports*, No. 45, April 1965, pp 69-73. This journal article utilized the im or iv route for methyl-glyoxal bis-guanylhydrazone (MGBG) 180, 250, or 350 mg/m$^2$ of surface area 2-3 times a week together with mercapto purine, the latter given orally 100 mg/m$^2$ per day or iv 250 mg/m$^2$ twice a week. This Boiron procedure is akin to the procedure of MGBG prevalent in the late 70's where the dosage required was multiple times per week or daily and the toxicity was excessive.

Knight, *Cancer Treatment Reports*, Vol. 63, No. 11-12, November/December 1979, pp 1933-37. This article embraces the technical area of the present invention and shows the key difference of weekly dosage regimen at 250-1,000 mg/m$^2$ per week.

DESCRIPTION OF THE PRIOR ART

The antitumor activity of methyl-glyoxal bis-guanylhydrazone (MGBG) in leukemia-L1210- and adenocarcinoma-755-bearing rodents was first reported by Freelander and French, 18 *Cancer Res.* 360 (1958). Subsequently, the antineoplastic activity was confirmed and extended to include other organ tumors whether in transplanted or normal tumor-bearing animals. After a phase of intensive preclinical and clinical investigations, significant activity against acute myelocytic leukemia was noted in human subjects receiving an average daily parenteral dose of 126 to 160 mg/m$^2$. The remission rate (45 percent complete remissions) reported by Levin et al., 6 *Clinical Pharmacol. Ther.* 31 (1965) was higher than that previously reported for other antitumor agents. Indeed this marked activity is reflected by the median increase in survival from 2.5 to 6.5 months when compared to patients with myeloblastic leukemia treated with 6-mercaptopurine.

Although clinical experience has shown MGBG to be unique in its chemotherapeutic management of malignant disease, enthusiasm for the drug's antileukemic powers was severely restrained by the occurrence of concomittant profound and protean toxicity associated with its administration. The toxicological effects of MGBG observed, some of which are peculiar to certain animal species, include gastrointestinal toxicity, delayed and fatal hypoglycemia, hepatic and renal damage, bone marrow depression, diarrhea and phlebitis. These effects, with the possible exception of renal and hepatic involvement, have also prevailed in human subjects undergoing MGBG treatment. Additionally, several toxic effects were demonstrated which are unique to man. These include esophagitis, ulcerative pharyngitis, laryngitis, stomatitis, genital mucosa swelling, conjunctivitis, mucositis, erythema, edema, desquamating dermatitis, and profound anorexia with associated weight loss. Patients who were administered MGBG on a daily schedule exhibited remission to acute leukemia only after a precarious struggle with the oftentimes life threatening side effects. In many patients, treatment had to be discontinued before any beneficial results could be noted.

TRIAL DOSAGE SCHEDULES IN ANIMALS

Although the initial studies in which animals received repeated parenteral doses of MGBG did not indicate dose-limiting side effects, toxicological effects observed clinically have been attributed to cumulative effects of repeated daily doses. This cumulation or accretion of toxicity is possibly explained by the unusually prolonged period required for urinary elimination of MGBG in man. Bioavailability studies in man with MGBG-C$^{14}$ have shown that following a single intravenous infusion over a period of 20 minutes, the radioactivity rapidly disappeared from the plasma and that over an extended period of 3 weeks approximately 60 percent of the drug was excreted unchanged in the urine. These data suggest that MGBG accumulates in the tissues and is slowly leached from tissue deposits to accomplish elimination.

On this bioavailability basis, studies were made and evaluated in an attempt to circumvent or modify the course of toxicity in man and improve the therapeutic index of MGBG. One course of treatment consisted of administering an initial high-loading dose of MGBG followed by daily lower-than-usual maintenance doses. Unfortunately, this series of treatments also proved unsuccessful in the few patients studied. Other schedules and combinations investigated also failed to improve the therapeutic index. For example, in one study MGBG was administered in combination with other neoplastic agents such as 6-mercaptopurine or the vinca alkaloids. These investigations indicated that any alteration in the effective dose range (126 to 160 mg per square meter per day) resulted in either more toxicity or decreased antitumor activity.

MECHANISM AS SHOWN IN IN VITRO EXPERIMENTS IN ANIMALS

Though the mechanism of MGBG antitumor action is still not elucidated, it has been postulated that MGBG exerts an inhibitory action relative to polyamine biosynthesis. Physiologically achievable effects of MGBG may be related to inhibition of the enzyme, S-adenosyl methionine decarboxylase, which catalyzes the synthesis of the polyamine, spermidine.

In vitro experiments have shown that MGBG in concentrations as low as 0.5 $\mu$g/ml is a potent inhibitor of spermidine biosynthesis. At intermediate concentrations (0.6-2.4 $\mu$g/ml) MGBG appears to act selectively on all polyamine synthesis. At concentrations as high as 30 $\mu$g/ml or more, the drug has other direct toxic effects, including inhibition of protein synthesis, and complete inhibition of mitochondrial respiration.

There is a growing body of evidence to suggest that spermidine, in particular, is of importance in the initiation of DNA synthesis, possibly through stabilization of the DNA polymerase-helix complex. Several studies have shown that MGBG-mediated depression of DNA synthesis is associated with spermidine depletion and putrescine accumulation. This conclusion is strengthened by the experimental reversal of DNA suppression when exogenous spermidine, in equimolar quantities as putrescine, is added to the culture study.

A second area in which polyamines play a major role is in RNA synthesis, especially that of transfer (t) RNA. The methylation of tRNA may be directly stimulated by polyamines, a finding of particular interest in light of the reports that neoplastic tissue differs from normal tissue with respect to the extent of methylated tRNA. Here, too, spermidine appears to play a critical role.

Polyamine accumulation appears to be a necessary requisite to DNA synthesis at an optimal rate, in both normal and neoplastic tissues. Thus, the toxicity of MGBG observed in tissues with rapid turnover (skin, G.I. mucosa, and bone marrow) may be directly related to inhibition of polyamine biosynthesis and a subsequent depletion of RNA and DNA, the agents which ultimately regulate cell replication. There is, however, strong evidence that: (1) polyamines are excreted in excess in the majority of cancer patients; (2) polyamines, especially spermidine, are released from tumor cells during and after effective chemotherapy, with an initial peak in excretion and in serum levels and subsequent drop toward normal values; and (3) chemotherapy which produces only bone marrow (or other normal tissue) toxicity, and is without antitumor effectiveness, does not produce a significant increase in polyamine excretion. The latter observation would suggest either that cancer cells have much higher levels of polyamines than normal cells, even those with higher rates of DNA synthesis, or that therapy which is effective produces rather specific effects on polyamine synthesis in cancer cells. Thus, the depletion of spirmidine is associated with the action of MGBG.

SUMMARY OF THE INVENTION

An important measure of therapeutic effectiveness of an antineoplastic agent is its ability to inhibit tumor growth while exhibiting a minimum of adverse side effects. It is therefore an object of this invention to increase the therapeutic index of MGBG by circumventing the prohibitive toxicity associated with a daily dosing schedule. Additionally, it is an object of this invention to affect favorable responses to a wide variety of solid tumors, particularly types known to be unresponsive to other chemotherapy.

THE DOSING SCHEDULE AND VARIATION IN THE THERAPEUTIC INDEX

In accordance with the present invention, a weekly dosing schedule was explored rather than the traditionally employed daily dosing schedule. As a result of this intermittant dosing schedule, a marked increase in the therapeutic index of MGBG was achieved. Moreover, antineoplastic activity was demonstrated to be effective in heretofore recalcitrant solid tumors, including colon, esophageal, renal cell, prostate, and breast carcinoma.

Although the relative incidence of toxic effects was significantly reduced over the prior art daily-dose regimen, that toxicity which did develop was for the most part unpredictable and seemed to be cumulative rather than dose related. This may be interpreted in part by the very limited pharmacologic data in man which suggests prolonged tissue retention and delayed excretion of primarily unmetabolized drug. Specifically, Oliverio, V. and Zubrod, C., 5 Ann. Rev. Pharmacol. 335–356 (1965) reported only 50% of an administered intravenous dose was excreted in the urine and less than 20% in the feces, over a three-week period.

DETAILED DESCRIPTION OF PREFERRED EMBODIMENTS

The following discussion is in terms of the preferred embodiments of this invention, which represent the best mode known to the inventor at the time of this application.

In accordance with the preferred embodiments of this invention, MGBG is the abbreviation for the generic compound, methyl-glyoxal bis-guanylhydrazone. The official IUPAC designation of MGBG is 1,1'-[(methylethanediylidene)dinitrilo] diguanidine, which is represented by the formula diagram:

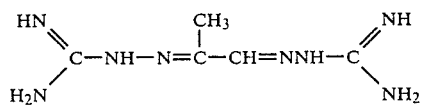

The molecular weight of the free drug is 184.21, with an elemental weight composition of 32.60% carbon, 6.57% hydrogen and 60.83% nitrogen. Spectral characteristics of MGBG include a $UV_{max}$ of 283 nm at pH 1 ($\epsilon=38,400$) and at pH 11 a $UV_{max}$ of 325 nm ($\epsilon=33,500$). Methods of preparation have been disclosed by Baiocchi et al., 6 J. Med. Chem. 431 (1963) and Oliverio, 52 J. Pharm. Sci. 202 (1963).

Further in accordance with the preferred embodiments of this invention, a pharmaceutically acceptable salt of MGBG was the active agent used in the clinical studies. It is necessary to administer MGBG in a salt form to assure solubility of drug in the administration of fluid such as 5% (w/v) dextrose in water. Additionally, the salt form must be administered to the subject to prevent the toxic effects associated with the drug-protein complexation and precipitation which result if the free-state drug is administered systemically. Available MGBG-salt complexes include but are not limited to the dihydrochloride (NSC-32946) and the diacetate (NSC-30689). Other pharmaceutically acceptable salt complexes which may be administered include the bisulfite and sulfate forms; however, these forms are not as soluble as the dihydrochloride or diacetate salts.

Methyl-glyoxal bis-guanylhydrazone (MGBG) is a potent antitumor agent. However, clinical use of the drug prior to this application has not been promoted since its use is associated with severe and often fatal toxicity. In accordance with the preferred embodiments of this invention, improved methods of administration have circumvented many of the profound toxic side effects such that clinical treatment of malignant disease with MGBG is a viable and even preferred alternative to other chemotherapeutic agents.

It is of importance in the consideration of the utility of the present invention that in 1977 it has been shown that the MGBG drug was practically unused due to the unsatisfactory toxicity associated with its use under the dosage schedule then in fashion. Under the weekly dosage schedule proposed by this invention, a dramatic improvement in lessening of toxicity has resulted.

Some of the clinical experiments of applicant are reported in the examples which follow:

EXPERIMENTAL TESTS OF METHODS OF INVENTION

During the course of the clinical experiments, MGBG was administered to patients in approximately weekly doses ranging from 250 to 1000 mg per square meter. This dosage range serves as the therapeutic effective dose when MGBG is administered in accordance with the presently described methods of treatment for advanced malignant disease.

For the purposes of analysis and in view of the desired objectives of this invention, the discussion of the results are divided into two segments, Response and Toxicity. The first topic, Response, discusses the wide spectrum usefulness of MGBG as administered in the specified manner. Additionally, this section illustrates encouraging results in the treatment of refractory colon, renal and pancreatic cancer. The second topic, Toxicity, demonstrates the improved therapeutic index of MGBG as a consequence of the improved schedule of treatment. Particularly, no toxic effects were noted in approximately 74% of the patients treated. This reflects a dramatic improvement over previous reports noting a toxicity occurrence in 80 to 100 percent of patients treated on a daily dosing schedule.

Patients were eligible for entry into the study concerning the improved method of treatment with MGBG if they had a pathologically documented diagnosis of malignant disease, were not eligible for participation in a study of higher priority within the Southwest Oncology Group (SWOG) and had measurable disease. Pre-treatment minimum evaluation included chest roentgenogram, liver and renal function tests, complete blood count with differential and platelet count and serum glucose. Pre-treatment performance status was recorded for each patient in accordance with SWOG criteria.

According to the methods of this invention, a therapeutically effective dose of MGBG in a pharmaceutically acceptable salt form such as the dihydrochloride (NSC-32946) or the diacetate (NSC-30689) salts (supplied by the National Cancer Institute, National Institutes of Health) is aseptically added to an intravenous infusion of a suitable vehicle such as 100 ml of 5% (w/v) dextrose and water for injection (available from such sources as Baxter-Travenol and Cutter Laboratories). This intravenous infusion is administered to the patient over a period of time not less than 30 minutes. Accordingly, an approximation of the patient's surface area in square meters is calculated using a height and weight to surface area nomogram (listed in Documenta Geigy, *Scientific Tables* (1970) p. 537) and this factor is applied in determining the appropriate amount of MGBG salt to be added to the infusion solution. The therapeutically effective dose of MGBG appears to fall within the range of 250–1000 mg/$m^2$ per week. Initially, the dosing schedule was 250 mg/$m^2$ weekly; however, this starting dose was subsequently increased to 500 mg/$m^2$ weekly after the first twelve patients demonstrated no toxicity and no response at 250 mg/$m^2$. In the absence of toxicity, subsequent doses of MGBG are increased by 100 mg/$m^2$ over the previous week's dose. If patients experience moderate or severe reversible toxicity, the dose is reduced by 100 mg/$m^2$ relative to the previous week's dose. No change in dosage strength is made for mild toxicity.

Response by disease category is summarized in Table I below.

TABLE I

| | | Response by Diagnosis | | | | | |
|---|---|---|---|---|---|---|---|
| Diagnosis | Number Evaluable | $CR^1 + PR^2$ | Duration Months | $CR^1$ | $PR^2$ | $IMP^3$ | No Response |
| Renal (13)* | 5 | 1 | 5 | | 1 | 2 | 2 |
| Colon (27) | 14 | 3 | 5, 5, 7+ | | 3 | | 11 |
| Pancreas (7) | 5 | 2 | 7+, 8+ | | 2 | | 3 |
| Lung (7) (non-small cell) | 6 | 2 | 2, 7+ | | 2 | | 4 |
| Esophagus (4) | 2 | 1 | 3 | | 1 | | 1 |
| Bladder (4) (transitional cell) | 3 | 1 | 1 | 1 | | | 2 |
| Adenocarcinoma (unknown primary) (4) | 3 | 1 | 2 | 1 | 1 | 1 | |
| Breast (18) | 12 | | | | | 2 | 10 |
| Lymphoma (6) | 2 | | | | | | 2 |
| Prostate (11) | 6 | | | | | 1 | 5 |
| Head & Neck (2) | 2 | | | | | | 2 |
| Hepatoma (2) | 1 | | | | | | 1 |
| Melanoma (1) | 1 | | | | | 1 | |
| Leukemia** (1) | 1 | | | | | 1 | |
| Ewings (1) | 1 | | | | | | 1 |
| Oat Cell (1) | 1 | | | | | 1 | |
| | 65 | 11 | | 2 | 9 | 9 | 45 |

*Number entered
**Patient received 1 mg/$m^2$ weekly for three weeks
$^1$CR - Complete response
$^2$PR - Partial response
$^3$IMP - Improvement noted

TOXICITY

Shortly after Freelander and French [*Cancer Res.* 18:360–363 (1958)] described the growth inhibiting effects of MGBG in mouse L 1210 leukemia, MGBG went through a phase of intensive preclinical and clinical investigation. Although MGBG was found to have major activity in acute myelocytic leukemia on a daily dosing schedule, its toxicity was diverse: mucositis, vasculitis, and profound anorexia with associated weight loss.

According to a report by Freireich et al, Cancer Chemotherapy Reports, 16:183–186 (1963) MGBG exhibits a very low therapeutic index when administered parenterally on a daily dosing schedule. Toxicity evaluation determined by Freireich et al, supra, at 186 are tabulated in Table II below.

TABLE II

Toxicity to MGBG (Freireich Study)

| Patient | Response | Days to first Toxicity | Dose rate (mg/m$^2$/day) | Toxic Manifestation |
|---|---|---|---|---|
| 1 | None | 16 | 230 | Thrombocytopenia |
| 2 | None | 7 | 340 | Gastrointestinal |
| 3 | Partial | 9 | 256 | Gastrointestinal |
| 4 | Complete | 7 | 264 | Gastrointestinal |
| 5 | Complete | 10 | 252 | Gastrointestinal |
| 6 | Complete | 10 | 156 | Gastrointestinal |
| 7 | Complete | 6 | 194 | Gastrointestinal |
| 8 | Complete | 7 | 194 | Gastrointestinal acrocellulitis |
| 9 | Partial | 23 | 150 | None |
| 10 | Complete | 24 | 150 | None |
| 11 | Complete | 15 | 150 | None |
| 12 | Complete | 13 | 150 | Gastrointestinal |
| 13 | Complete | 13 | 150 | None |

In a later study by Regelson and Holland [Cancer Chemotherapy Reports, 27:15 at 15 (1963)] response to MGBG "was seen only in the presence of significant toxicity which seriously compromised any clinical improvement." Table III summarizes the toxicity noted from intravenously administered MGBG at 150 mg/m$^2$/day over 63 courses in 46 patients (Regelson et al, supra at 23).

TABLE III

Toxicity to MGBG (Regelson Study)

| Toxicity | No. of Patients* |
|---|---|
| Oropharyngeal and/or esophageal | 43 |
| Diarrhea | 32 (1) |
| Cutaneous lesions | 12 |
| "Myositis" | 5 |
| (Lymphomas and solid tumors) | |
| Leukopenia <3000 mm$^3$ | 5 (1) |
| Thrombocytopenia <75,000/mm$^3$ | 3 |
| (Acute leukemia) | |
| Leukopenia <3000/mm$^3$ or <50% of initial value | 16 (1) |
| Hypoglycemia <60 mg % | 4 (2) |
| Laryngitis | 14 (1) |
| Proctitis | 2 |
| Vulvovaginitis | 4 |

*Numbers in parentheses indicate severe toxicity, which contributed to the death of 6 of 27 patients who dies while on study.

In evaluating the therapeutic index associated with the daily administration of MGBG, Regelson et al, "believe that because of its toxicity and short duration of objective anti-tumor effects, it does not merit therapeutic acceptance at the schedules and doses we have used." (Regelson et al, supra at 25).

Another clinical evaluation of MGBG treatment involving parenteral daily dosing was conducted by the National Cancer Institute, [Levin et al, Clinical Pharmacology and Therapeutics 6:31-42 (1965)]. MGBG was administered in average daily doses ranging from 45 to 300 mg/m$^2$. The patients were divided into four groups based on the average dose per day. Group I patients received less than 100 mg/m$^2$/day. Group II subjects received an average daily dose of 100 to 125 mg/m$^2$. Group III patients received an average daily dose of 126 to 160 mg/m$^2$. Group IV patients received over 160 mg/m$^2$/day.

Table IV summarizes the toxic manifestations noted by Levin et al, supra at 38-39.

TABLE IV

| Toxicity[2] | Group I (12)[1] | Group II (23) | Group III (36) | Group IV (12) |
|---|---|---|---|---|
| Mucosal involvement | 80% (8) | 98% (15) | 91% (31) | 100% (10) |
| Penile inflammation[3] | (0) | 25% (3) | 23% (4) | (0) |
| Diarrhea | 40% (4) | 41% (6) | 42% (15) | 20% (2) |
| Vasculitis | 40% (4) | 25% (5) | 25% (8) | 20% (2) |
| Acroerythema | (0) | 17% (4) | 17% (6) | 20% (2) |
| Erythema Nodosum | 10% (1) | 9% (2) | 12% (3) | (0) |
| Weight Loss (Median %) | 0 | 6% | 10% | 5% |
| Died during treatment | 42% (5) | 62% (10) | 30% (11) | 83% (10) |

[1]Number in parenthesis indicates number of patients.
[2]Percentages are based on patient population surviving at least 5 days.
[3]Percentage is based on male population.

The National Cancer Institute's experience with a daily dosing regimen with MGBG lead to the conclusion that the severe toxicity associated with MGBG administration indicated a need for continued efforts to modify the complications. In this regard, Levin et al investigated other schedules of administration including continuous 24-hour infusion of MGBG and initial treatment with a very high dose followed by lower maintenance doses. However, neither of these regimens altered the incidence of associated toxicity demonstrated by the daily dosing studies.

Previous trials of MGBG given on a daily schedule were associated with prohibitive toxicity. Applicant explored a weekly schedule and found a marked increase in the therapeutic index of MGBG.

Of 109 patients receiving MGBG, 12 received only 250 mg/m$^2$, a dose which produced no apparent biologic effect, and 7 were lost to followup. Information regarding toxicity is reported for 90 patients who received 500 mg/m$^2$ or more each week.

Of these 90 patients, 67 (74%) had no toxicity and this is in direct contrast to the prior art. The major toxicity encountered was mucositis, which was seen in 17 (19%) patients. One drug-related death secondary to mucositis was seen in a patient with hepatoma who received one dose of MGBG at 600 mg/m$^2$. This patient had normal pre-treatment hepatic and renal function, without ascites or effusion. The other prominent side effect was nausea and vomiting in 14 patients (16%). Myelosuppression was seen in only 7 patients (8%), and anemia in 3 (3%). The type and degrees of toxicity are summarized in Table V.

Severe muscle pain and weakness of the lower extremities was seen in three patients. Creatinine phosphokinase and aldolase was normal in all three. Muscle biopsy was not obtained. In each case this muscle pain and weakness was reversible with drug withdrawal. All three patients had previously received vinca alkaloids. One of these patients with acute leukemia developed this syndrome after three weekly doses of 1 mg/m$^2$.

Overall, toxicity appeared to be cumulative, as patients who received increasing numbers of courses experienced more toxicity (Table VI).

TABLE V

Toxicity (90 Patients)

| Toxic Effect | No. of Patients (Approx. %) |
| --- | --- |
| Mucositis | 17 (19) |
| erythema | 3 |
| ulcers, able to eat | 7 |
| ulcers, unable to eat | 6 |
| drug-related death | 1 |
| Nausea and vomiting | 14 (16) |
| nausea, no vomiting | 5 |
| vomiting $\leq 6$ times/day | 5 |
| vomiting $\geq 7$ times/day | 3 |
| hospitalization secondary to vomiting | 1 |
| Anorexia | 7 (8) |
| Diarrhea | 3 (3) |
| 3-4 stools/day, no dehydration | 1 |
| 4 liquid stools/day, IV hydration required | 1 |
| bloody diarrhea | 1 |
| Vasculitis | 2 (2) |
| Myopathy | 3 (3) |
| Balanitis | 4 (4) |
| Urethritis | 3 (3) |
| Skin rash | 2 (2) |
| Hematologic | 10 (11) |
| Anemia | |
| Hemoglobin (g/100 ml) | |
| 7.0-8.9 | 1 |
| 5.0-6.9 | 2 |
| Platelets: $25 \times 10^3$-$50 \times 10^3$/mm$^3$ | 2 |
| Granulocytes: $<1500$ mm$^3$ | 2 |
| $<1000$/mm$^3$ | 3 |

TABLE VI

| | Cumulative Toxicity | |
| --- | --- | --- |
| Number of Courses MGBG | Number of Patients | Number with Toxicity (Approx %) |
| 1 | 13 | 1 (8) |
| 2 | 25 | 7 (28) |
| 3 | 15 | 6 (40) |
| $\geq 4$ | 56 | 28 (50) |

SUMMARY OF IMPROVEMENT IN HERETOFORE TOXICITY OF MGBG

The results of these clinical investigations confirm the desired objectives that MGBG administered at weekly intervals is an effective chemotherapeutic agent which produces significant improvement in various cancer pathologies while exhibiting a higher therapeutic index than that previously documented concerning a daily dosing schedule. Applicant has demonstrated that administration of MGBG on a weekly schedule is associated with minimal, acceptable toxicity. Furthermore, favorable responses were achieved in a wide variety of solid tumors, particularly types known to be unresponsive to chemotherapy. Based on these observations, administration of MGBG at weekly intervals represents a significant improvement over the previously reported but disappointing daily dosing schedule employed in the treatment of advanced malignant disease.

While the invention has been described in terms of preferred embodiments constituting the best mode known to the applicant at the time of this application, various changes may be made in the invention without departing from the scope thereof, which is defined by the following claims.

I claim:
1. A method for reducing the toxic effects of methyl-glyoxal bis-guanylhydrazone in a patient comprising:
administering to said patient at approximately weekly intervals a therapeutically effective dose ranging from about 250 mg/m$^2$ to about 1000 mg/m$^2$ of methyl-glyoxal bis-guanylhydrazone in its pharmaceutically acceptable salt form, dispersed in a suitable physiologically compatible vehicle.
2. The method according to claim 1 wherein an initially effective dose at Week 1 is about 250-350 mg/m$^2$ of body surface.
3. The method according to claim 1 wherein a therapeutically effective dose range from about 500 mg/m$^2$ to about 600 mg/m$^2$ of body surface is utilized.

* * * * *